United States Patent [19]
Bishop et al.

[11] Patent Number: 5,981,500
[45] Date of Patent: Nov. 9, 1999

[54] ANTIPARASITIC AGENTS RELATED TO THE MILBEMYCINS AND AVERMECTINS

[75] Inventors: Bernard Frank Bishop; Michael Stephen Pacey, both of Sandwich, United Kingdom; David Austen Perry, Groton, Conn.

[73] Assignee: Pfizer Inc., New York, N.Y.

[21] Appl. No.: 08/853,686

[22] Filed: May 9, 1997

Related U.S. Application Data

[63] Continuation of application No. 08/491,935, filed as application No. PCT/EP94/00095, Jan. 12, 1994, abandoned.

[51] Int. Cl.⁶ ............................. A61K 31/70; C07H 17/08
[52] U.S. Cl. ................................ 514/30; 514/27; 514/28; 536/7.1
[58] Field of Search ................. 536/7.1; 514/30, 514/27, 28

[56] References Cited

U.S. PATENT DOCUMENTS

| | | | |
|---|---|---|---|
| 5,055,454 | 10/1991 | Blizzard et al. | 514/30 |
| 5,055,596 | 10/1991 | Baker et al. | 549/268 |
| 5,169,839 | 12/1992 | Linn et al. | 514/30 |

FOREIGN PATENT DOCUMENTS

| | | |
|---|---|---|
| 379341 | 5/1990 | European Pat. Off. . |
| 353959 | 7/1990 | European Pat. Off. . |
| 411897 | 2/1991 | European Pat. Off. . |
| 428285 | 5/1991 | European Pat. Off. . |
| 428286 | 5/1991 | European Pat. Off. . |
| 480693 | 4/1992 | European Pat. Off. . |
| 506331 | 9/1992 | European Pat. Off. . |
| 519731 | 12/1992 | European Pat. Off. . |
| 535734 | 12/1992 | European Pat. Off. . |

*Primary Examiner*—Elli Peselev
*Attorney, Agent, or Firm*—Peter C. Richardson; Paul H. Ginsburg; Gezina Holtrust

[57] ABSTRACT

A 5-oximino-25-substituted avermectin B1 or B2 monosaccharide of formula I herein has use in the treatment of parasitic infections in animals and humans. The compounds may be prepared from corresponding 5-keto substituted derivatives.

11 Claims, No Drawings

ANTIPARASITIC AGENTS RELATED TO THE MILBEMYCINS AND AVERMECTINS

This is a continuation of application Ser. No. 08/491,935, filed on Jun. 22, 1995, now abandoned, which is a 371 of PCT/EP 94/00095 filed Jan. 12, 1994.

This invention relates to new antiparasitic agents, related to the milbemycins and avermectins and to processes for their preparation and compositions thereof.

The avermectins are a group of broad spectrum antiparasitic agents referred to previously as the C-076 compounds. They are produced by fermenting a strain of the microorganism *Streptomyces avermitilis* under aerobic conditions in an aqueous nutrient medium containing inorganic salts and assimilable sources of carbon and nitrogen. The isolation and the chemical structure of the eight individual components which make up the C-076 complex is described in detail in British Patent Specification 1573955.

The C-076 complex comprises eight distinct but closely related compounds described as C-076 A1a, A1b, A2a, A2b, B1a, B1b, B2a and B2b. The "a" series of compounds refers to the natural avermectins wherein the 25-substituent is (S)-sec-butyl and the "b" series to those wherein the 25-substituent is isopropyl. The designations "A" and "B" refer to avermectins wherein the 5-substituent is methoxy or hydroxy, respectively, and the numeral "1" refers to avermectins wherein a double bond is present at the 22-23 position, and numeral "2" to avermectins lacking the 22-23 double bond and having a hydrogen at the 22-position and hydroxy at the 23 position.

In our European Patent Applications 0214731, 0284176, 0317148, 0308145, 0340832, 0335541 and 0350187 there are described preparations of compounds related to the avermectins but having a group at the 25-position other than the isopropyl or (S)-sec-butyl groups found in the original avermectin compounds disclosed in British Patent Specification 1573955. Such compounds may be prepared by fermentation of particular strains of *Streptomyces avermitilis* in the presence of organic acids or derivatives thereof. Production of such avermectins is described in Journal of Antibiotics (1991), 44, No. 3, pp 357–365.

The milbemycins form another group of related macrolides which are distinguished from the avermectins in lacking a sugar residue attached at the C-13 position. Examples of such compounds are described in UK patent 1390336, and European patent publications 170006, 254583, 334484 and 410615. In addition to these fermentation products a large number of publications describe compounds derived semisynthetically from these fermentation products many of which possess useful antiparasitic activities. Some of this chemistry is reviewed in *Macrolide Antibiotics,* Omura S., Ed., Academic press, New York (1984) and by Davies, H. G., Green, R. H. in *Natural product Reports* (1986), 3, 87–121 and in Chem. Soc. Rev., 1991, 2, 271–339.

It has been found that certain compounds synthetically derivable from known avermectins and avermectin derivatives possess unexpected beneficial biological properties.

According to one aspect of the invention there are provided compounds of formula (I):

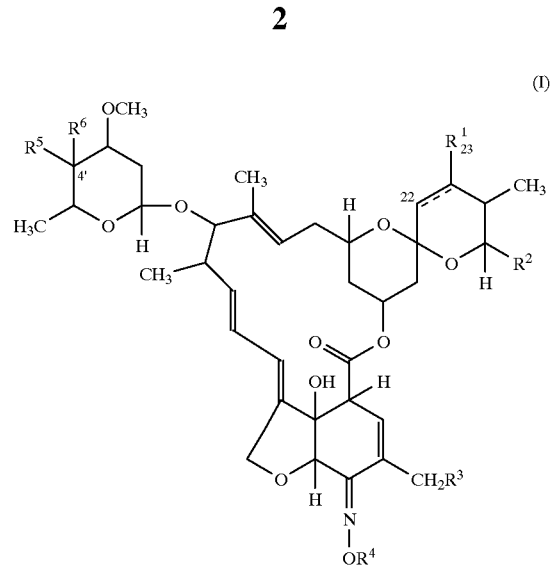

wherein the broken line at the 22-23 position represents an optional bond and either this bond is present and $R^1$ is absent or this bond is absent and $R^1$ is H, OH, oxo or oximino optionally substituted by a $C_1$–$C_8$ alkyl group, $R^2$ is a $C_1$–$C_8$ alkyl, $C_2$–$C_8$ alkenyl or $C_3$–$C_8$ cycloalkyl group, or a 3- to 6- membered heterocyclic ring containing a sulphur or oxygen atom, said ring being saturated or fully or partially unsaturated and optionally substituted by one or more $C_1$–$C_4$ alkyl groups or halogen atoms, $R^3$ is H or OH, and $R^4$ is H or a group capable of being hydrolysed in vivo to yield a compound in which $R^4$ is H, $R^5$ is OH, optionally substituted with a group capable of being hydrolysed in vivo to yield a compound in which $R^5$ is OH.

and $R^6$ is H or $C_1$–$C_4$ alkyl, or $R^6$ is H and $R^5$ is amino, optionally substituted with at least one group selected from $C_1$–$C_8$ alkyl and acyl (which may be alkanoyl) groups.

Unless the context otherwise requires, all alkyl and alkenyl substituents having 3 or more carbon atoms may be straight or branched-chain. The term "aryl" includes phenyl which may be substituted by at least one $C_1$–$C_6$ alkyl, hydroxy, $C_1$–$C_6$ alkoxy, halo, nitro or $CF_3$ group. In the present invention the term "alkyl" is intended to indicate those alkyl groups of from 1 to 8 carbon atoms such as methyl, ethyl, propyl, isopropyl, butyl, pentyl, hexyl, and the like, either straight or branched chain. The term "alkanoyl" is intended to include those alkanoyl groups of from 1 to 8 carbon atoms such as formyl, acetyl, propionyl, buytryl, pentanoyl, hexanoyl, and the like.

The term "carbamoyl" is intended to indicate the group —$CONR_7R_8$ where $R_7$ and $R_8$ are the same or different and are H, alkyl, aryl, heteroaryl or from a 4–8 membered ring containing 1 or more O, N, or S atoms.

The above structural formula is shown without a definitive stereochemistry. However, during the course of the synthetic procedures used to prepare such compounds, the products of such procedures can be a mixture of stereoisomers. In particular, the stereoisomers at the 4"-, 4'-, 5, 13- and 23-positions may be oriented either α- or β-representing such groups being below or above the general plane of the molecule, respectively. In each of such case both the α- and β-configurations are intended to be included within the ambit of this invention. In certain cases the term "epi" is used to distinguish the stereoisomer being of opposite configuration to the natural compound at one specific asymmetrical carbon atom.

Groups hydrolysable in vivo to yield corresponding compounds in which the group is replaced by H are well known in the pharmaceutical art in general and a wide variety of such groups are suitable for use in the compounds of this invention. Examples of such groups are $C_2$–$C_8$ alkanoyl, aroyl, carbamoyl, $C_1$–$C_8$ alkoxycarbonyl groups, and dicarboxylic acid and amino acid residues. Particular groups are identified in the Examples below. Preferred compounds are those in which $R^2$ is a straight or branched $C_1$–$C_8$ alkyl or cycloalkyl group, such as cyclohexyl, isopropyl or sec-butyl, $R^3$ is H, and the optional bond at the 22-23 position is present or this optional bond is absent and $R^1$ is H or OH.

The oxime monosaccharides in which $R^3$ and $R^4$ are H are particularly preferred.

Individual compounds within the invention are described in the Examples given below.

The most preferred compound is 5-oximino-22,23-dihydro-25-cyclohexyl avermectin B1 monosaccharide.

According to another aspect of the invention, there is provided a process for preparing such a compound which comprises the steps (1) of oxidising a compound of formula (II):

(II)

wherein the broken line, $R^1$, $R^2$, $R^3$ and $R^6$ are as defined above and $R^5$ is as defined above or $R^5$ is α-oleandrosyl oxy and $R^6$ is H to yield a compound of formula (III):

(III)

and (ii) allowing the compound of formula (III) to react with a compound of formula $R^4$—O—$NH_2$ where $R^4$ is as defined above and where $R^5$ is α-oleandrosyl oxy, hydrolysing the compound obtained to yield a compound of formula (I), and (iii) if necessary replacing group $R^4$ when the latter is H with said group capable of being hydrolysed in vivo to yield a compound in which $R^4$ is H, if necessary, the process further comprising one or more of the following steps before or after steps (i), (ii) and (iii), (iv) substituting group $R^5$ when the latter is OH with said group capable of being hydrolysed in vivo to yield a compound in which $R^5$ is OH, (v) oxidising group $R^1$ when the latter is OH to oxo, (vi) reacting the compound obtained from step (v) with hydroxylamine optionally substituted by a $C_1$–$C_8$ alkyl group to yield a compound in which $R^1$ is optionally substituted oxo, (vii) hydrogenating the compound to reduce a double bond at the 22-23 position to a single bond, (viii) oxidising a compound in which $R^3$ is H to a compound in which $R^3$ is OH, (ix) oxidising a compound in which $R^5$ is OH and $R^6$ is H to a compound in which $R^5$ is oxo and $R^6$ is absent, and either:

(x) reducing the compound obtained from (ix) to produce a compound in which $R^5$ is an epi-OH group, or (xi) reacting the compound obtained from (ix) with a Grignard reagent to yield a compound in which $R^5$ is OH and $R^6$ is alkyl, or (xii) subjecting the compound obtained from (ix) to reductive amination to yield a compound in which $R^5$ is an amino or alkylamino group, and if necessary acylating the compound obtained, any free OH groups being protected if necessary during any of the above steps.

Preparation of compounds according to the invention is discussed, by way of illustration, below.

The compounds of the present invention may be prepared starting from the compounds of formula (iv), which may themselves be prepared as described in the above-mentioned patent publications.

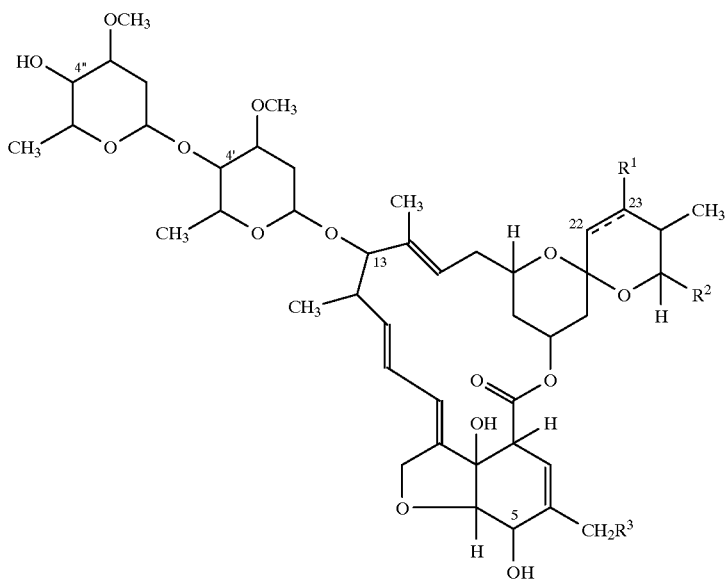

(II)

Compound IIa Double bond present, $R^1$ absent.
Compound IIb Double bond absent, $R^1$ = H.
Compound IIc Double bond absent, $R^1$ = OH.

The semisynthetic modifications required to provide the compounds given by formula I may require sequential reactions at the positions –4', 4", 1, 4a, 13, 22, 23, 25 and 5 and the exact order in which these transformations are performed may vary. In addition, during the oxidation and certain substitution reactions described below, it is necessary to protect the 5-hydroxy group to avoid substitution or oxidation at that position. With this position protected, the reactions may be carried out at the 4"-, or 4'-positions without affecting the remainder of the molecule. Subsequent to any of the above-described reactions, the protecting group may be removed and the unprotected product isolated. For compounds of this invention, conversion of the 5-hydroxy group to a ketone or ketoxime is preferably performed after substitution at the 4', 23 and 4a positions. The protecting group employed at the 5-position is ideally one which may be readily synthesized, will not be affected by the reactions at the 4"- and 4'-positions and may be removed without affecting any other functionality of the molecule. One preferred type of protecting group of the avermectin type of molecule is the tri-substituted silyl group, preferably the tri-loweralkyl silyl group. One especially preferred example is the tert.-butyldimethylsilyl group. The reaction preparing the protected compound is carried out by reacting the hydroxy compound with the appropriately substituted silylhalide, preferably the silylchloride in an aprotic solvent such as methylene chloride, benzene, toluene, ethyl acetate, tetrahydrofuran, dimethylformamide and the like. In order to minimise side reactions, there is included in the reaction mixture a base to react with the acid released during the course of the reaction. Preferred bases are amines such as imidazole, pyridine, or triethylamine. The base is required in amounts equimolar to the amount of hydrogen halide liberated; however, generally several equivalents of the amine are employed. The reaction is stirred at from 0° C. to the reflux temperature of the reaction mixture and is complete in from ½ to 16 hours. The silyl group is removed by treatment of the silyl compound with anhydrous pyridine-hydrogen fluoride in tetrahydrofuran. The reaction is complete in from 3 to 24 hours at from 0 to 25° C. Alternatively, the silyl group may be removed by stirring the silylated compound in methanol catalyzed by an acid preferably a sulfonic acid monohydrate such as p-toluenesulfonic acid monohydrate. The reaction is complete in about 1 to 12 hours at from 0 to 50° C. Compounds having a 23-hydroxyl group (or a protected derivative) may be converted to either the corresponding 22,23-dihydro compound or alternatively to the corresponding compound having a double bond at the 22-23 position using methods described in U.S. Pat. No. 4,328,335. The latter compounds may also be hydrogenated to the 22,23-dihydro compounds using Wilkinson's catalyst under conditions described in U.S. Pat. No. 4,199,569.

The preparation of the compounds of the invention can be accomplished by first converting the aforementioned disaccharides IIa, b and c into their corresponding monosaccharides by hydrolysis. An alternative method of preparing the monosaccharides comprises a direct fermentation procedure starting from a corresponding aglycone as described in European Patent Application 463677. The 5-hydroxy position is then protected to avoid substitution at this position so that reaction may be carried out at the 4', or 23 positions. The 4'-hydroxy is more reactive than the 23-hydroxy, hence additional suitable protection at C-4' allows selective reaction at C-23.

Alternatively, the compounds of the invention may be prepared by carrying out the above synthetic manipulations on the disaccharides IIa, b or c and finally hydrolysing them to the desired monosaccharides.

When desired, hydroxy groups may be acylated to give esters using reagent such as acid anhydrides or acid chlorides and amine bases according to general procedures known to those skilled in the art. Hydroxy groups may be converted to oxo groups by oxidation with manganese dioxide or tetrapropylammonium perruthenate. The oxo compound may be treated with hydroxylamine or an O-substituted analogue thereof to produce the corresponding oxime.

Compounds in which $R^3$ is OH are prepared from suitably 5-protected derivatives by firstly hydroxylating the 4a methyl group using a procedure described in the Japanese Patent Laid-Open Patent Application No. 83-59988.

Compounds in which $R^5$ is an amino group optionally substituted by one or more alkyl or acyl groups, may be prepared by reduction amination of a corresponding compound in which $R^5$ is oxo, for example by reaction with an ammonium salt or amine salt and sodium cyanoborohydride in known manner. The amino group may then be further substituted, by acetylation, for example using acetic anhydride.

Compounds in which $R^5$ is an epi-OH group may be made by reduction of such an oxo compound. The oxo compound may be converted to a compound in which $R^5$ is OH and $R^6$ is alkyl by reaction with a Grignard reagent in known manner.

The compounds of the invention are effective in treating a variety of conditions caused by endoparasites including, in particular, helminthiasis which is most frequently caused by a group of parasitic worms described as nematodes and which can cause severe economic losses in swine, sheep, horses and cattle as well as affecting domestic animals and poultry. The compounds are also effective against other nematodes which affect various species of animals including, for example:- Dirofilaria in dogs and various parasites which can infest livestock, companion animals such as cats and dogs and also humans including gastrointestinal parasites such as Ancylostoma, Necator, Ascaris, Strongyloides, Trichinella, Capillaria, Toxocara, Toxascaris, Trichuris, Enterobius and parasites which are found in the blood or other tissues and organs such as filarial worms and the extra intestinal stages of Strongyloides, Toxocara and Trichinella.

The compounds are also of particular value in treating ectoparasite infections including particular arthropod ectoparasites of humans, animals and birds such as ticks, mites, lice, fleas, blowfly, biting insects and migrating dipterous larvae which can affect cattle and horses.

The compounds are also insecticides active against household pests such as the cockroach, clothes moth, carpet beetle and the housefly as well as being useful against arthropod pests of stored grain and of agricultural plants such as spider mites, aphids, caterpillars and against migratory orthopterans such as locusts. We have discovered that compounds within the scope of this invention are both safe and have unexpectedly high potent systemic activity against fleas and other important arthropod parasites of cats and dogs.

The compounds of formula (I) may be administered as a formulation appropriate to the specific use envisaged and to the particular species of host animal being treated and the parasite or insect involved. The compounds may be administered by injection, either subcutaneously or intramuscularly, alternatively they may be administered orally in the form of a capsule, bolus, tablet, chewable tablet or liquid drench, or they may be administered as a topical formulation or as an implant. For topical application dip, spray, powder, dust, pour-on, spot-on, jetting fluid, shampoos, collar, tag or harness may be used. Such formulations are prepared in a conventional manner in accordance with standard veterinary practice. Thus capsules, boluses or tablets may be prepared by mixing the active ingredient with a suitable finely divided diluent or carrier, additionally containing a disintegrating agent and/or binder such as starch, lactose, talc, or magnesium stearate. A drench formulation may be prepared by dispersing the active ingredient in an aqueous solution together with dispersing or wetting agents and injectable formulations may be prepared in the form of a sterile solution or emulsion. Pour-on or spot-on formulations may be prepared by dissolving the active ingredient in an acceptable liquid carrier vehicle, such as butyl digol, liquid paraffin or non-volatile ester with or without addition of a volatile component such as isopropanol. Alternatively, pour-on, spot-on or spray formulations can be prepared by encapsulation to leave a residue of active agent on the surface of the animal. These formulations will vary with regard to the weight of active compound depending on the species of host animal to be treated, the severity and type of infection and the body weight of the host. The compounds may be administered continuously, particularly for prophylaxis, by known methods. Generally for oral, parenteral and pour-on administration a dose of from about 0.001 to 10 mg per kg of animal body weight given as a single dose or in divided doses for a period of from 1 to 5 days will be satisfactory but of course there can be instances where higher or lower dosage ranges are indicated and such are within the scope of this invention.

As an alternative the compounds may be administered with the animal feedstuff and for this purpose a concentrated feed additive or premix may be prepared for mixing with the normal animal feed.

For use as an insecticide and for treating agricultural pests the compounds are applied as sprays, dusts, pour-on formulations, emulsions and the like in accordance with standard agricultural practice.

For human use the compounds are administered as a pharmaceutically acceptable formulation in accordance with normal medical practice.

The preparation of compounds according to the invention are illustrated by the following Examples.

EXAMPLE 1

22,23-Dihydroavermectin B1a monosaccharide 22,23-Dihydroavermectin B1a (50 g) was dissolved in a mixture of isopropanol (100 ml) and sulphuric acid (1 ml) and stirred at room temperature under a nitrogen atmosphere for 48 hours. The reaction mixture was poured onto crushed ice and extracted with dichloromethane (2×200 ml). The combined extracts were washed with aqueous saturated sodium bicarbonate solution (100 ml), dried over anhydrous magnesium sulphate and concentrated under vacuum to give white crystals (14 g) which were removed by filtration. Mass and NMR spectra were fully consistent with the proposed structure.

The B1b analogue was obtained by an identical method starting from 22,23-dihydroavermectin B1b.

EXAMPLE 2

5-Oxo-22,23-dihydroavermectin B1a monosaccharide 22,23-dihydroavermectin B1a monosaccharide (14 g) was dissolved in diethyl ether (200 ml) and activated manganese dioxide (14 g) added. The mixture was stirred at room temperature for 4 hours, filtered and evaporated to dryness under vacuum to yield the title product (11.4 g) whose NMR spectrum was fully consistent with the proposed structure.

The B1b analogue was obtained by an identical method starting from 22,23-dihydroavermectin B1b monosaccharide.

EXAMPLE 3

5-Oximino-22,23-dihydroavermectin B1a monosaccharide

5-Oxo-22,23-dihydroavermectin B1 a monosaccharide (1 g) was dissolved in dry pyridine (25 ml) and hydroxylamine hydrochloride (1 g) added. The stirred reaction mixture was heated under reflux for 4 hours and after cooling poured onto crushed ice and extracted with dichloromethane (2×50ml). The combined extracts were dried over anhydrous magnesium sulphate and evaporated under vacuum to give a crude gum (1.1 g). This material was purified using high pressure liquid chromatography on a Dynamax (trade mark) column (41.4×250 mm, 8 μm, ODS-silica, Rainin) eluting with methanol - water 83:17 at 42 ml per minute. Appropriate fractions were combined and evaporated to dryness to yield the title product as a white solid, melting point 180°–190° C. Mass and NMR spectra were fully consistent with the proposed structure.

5-Oximino-22,23-dihydroavermectin B1b was prepared by an identical method starting from 5-oxo-22,23-dihydroavermectin B1b monosaccharide.

EXAMPLE 4

22,23-Dihydro-25-cyclohexylavermectin B1 monosaccharide

25-Cyclohexylavermectin B1 (9.9 g) was dissolved in toluene (1 liter) and Wilkinson's catalyst (tris (triphenylphosphine)rhodium(I) chloride) (9.25 g) was added. The solution was hydrogenated on a large Parr (trade mark) shaker at room temperature at 50 psi hydrogen pressure. After 3 hours the reaction vessel was depressurised and allowed to stand for 12 hours before addition of a further portion of catalyst (5 g) and hydrogenated as before for a further 2 hours after which no starting material remained. The solution was filtered, evaporated to dryness under vacuum and the residue chromatographed on silica eluting with dichloromethane then dichloromethane:methanol 9:1. The crude product was then chromatographed again on silica (200 g) eluting with dichloromethane:methanol 19:1 to give after evaporation of the solvent under vacuum impure 22,23-dihydro-25-cyclohexylavermectin B1 as a brown foam (10 g). This material was dissolved in a mixture of isopropanol (200 ml) and sulphuric acid (2 ml) and the brown solution was stirred at room temperature for 15 hours then poured into a mixture of ice and water (500 ml) and extracted with dichloromethane (3×200ml). The organic layer was washed with saturated aqueous potassium hydrogen carbonate solution (100 ml), water (2×50 ml) dried over anhydrous magnesium sulphate and evaporated under vacuum to give a crude gum which was chromatographed on silica (100 g) eluting with dichloromethane then dichloromethane:ethyl acetate 2:1 to give the title compound (8.2 g). Mass and NMR spectra were fully consistent with the proposed structure.

EXAMPLE 5

5-Oximino 22,23-dihydro-25-cyclohexyavermectin B1 monosaccharide 22,23-Dihydro-25-cyclohexylavermectin B1 monosaccharide (8.2 g) was oxidized to the 5-oxo derivative using manganese dioxide in anhydrous diethyl ether according to the procedure of Example 2. The crude product was purified by chromatography on silica (50 g) to give the 5-oxo compound (3.22 g) as a yellow foam. This was dissolved in anhydrous pyridine (60 ml) and hydroxylamine hydrochloride (3.22 g) was added. After stirring for 15 hours at room temperature a further aliquot of hydroxylamine hydrochloride (3.22 g) was added and the solution heated to 50° C. until no starting material remained. The solution was poured into water (50 ml) and extracted with diethyl ether (3×50 ml). The organic layer was washed with water, saturated sodium chloride solution, dried over anhydrous sodium sulphate and evaporated to dryness under vacuum. The crude product was chromatographed on silica (25 g) eluting with dichloromethane: ethyl acetate 4:1 and finally purified by high pressure liquid chromatography using a Dynamax (trade mark) column (41.4×250 mm, 8 μm ODS-silica, Rainin) eluting with methanol:water 9:1 at 65 ml per minute. Appropriate fractions were combined and evaporated under vacuum to give the title compound (1.53 g). Mass and NMR spectra were fully consistent with the proposed structure.

EXAMPLE 6

25-Cyclohexylavermectin B2 monosaccharide

25-Cyclohexylavermectin B2 (10 g) was suspended in isopropanol (100 ml) and a solution of sulphuric acid (2 ml) in isopropanol (100 ml) was added. After stirring at room temperature for 24 hours the clear solution was poured into ice (600 g) and extracted with dichloromethane (2×100 ml). The organic layer was dried over anhydrous sodium sulphate and evaporated to dryness. The residue was dissolved in tetrachloromethane and the solution stored at 4° C. The crystals which separated slowly were periodically removed by filtration and found to be the pure title compound. Mass and NMR spectra were fully consistent with the proposed structure.

EXAMPLE 7

5-Oximino-25-cyclohexylavermectin B2 monosaccharide

Using the procedures of Examples 2 and 3, 25-cyclohexylavermectin B2 monosaccharide was converted to the title compound. Mass and NMR spectra were fully consistent with the proposed structure.

EXAMPLE 8

25-Cyclohexylavermectin B1 monosaccharide

25-Cyclohexylavermectin B1 (20 g) was dissolved in tetrahydrofuran (250 ml) and a mixture of tetrahydrofuran (250 ml), water (10 ml) and sulphuric acid (10 ml) was added. The mixture was stirred at room temperature for 15 hours then poured into a mixture of ice (500 g) and water (1 l) and extracted with dichloromethane (2×500 ml). The organic layer was washed with saturated aqueous sodium chloride solution, dried over anhydrous sodium sulphate and evaporated under vacuum to give a foam. This was chromatographed on silica (150 g) eluting with ethyl acetate - dichloromethane 1:1 to give a crude product (13.3 g). Final purification was achieved by reverse phase hplc using a Dynamax (trade mark) column (41.4×250mm, 8 μm ODS-silica, Rainin) eluting with methanol-water 4:1 at 70 ml per minute to give the pure title compound. Mass and NMR spectra were fully consistent with the proposed structure.

EXAMPLE 9

5-Oximino-25-cyclohexylavermectin B1 monosaccharide

Using the procedures of Examples 2 and 3, 25-cyclohexylavermectin B1 monosaccharide was converted to the title compound. Mass and NMR spectra were fully consistent with the proposed structure.

EXAMPLE 10

5-O-t-Butyldimethylsilyl-25-cyclohexyl-22,23-dihydroavermectin B1 monosaccharide 22,23-dihydro-25-cyclohexyl-avermectin B1 monosaccharide (Example 4) (12.1 g) and imidazole (7.2 g) were dissolved in dry dimethylformamide (10 ml). To this solution at room temperature was added t-butyldimethylsilyl chloride (7.9 g). After 18 hours the mixture was poured into ice-water (200 ml) acidified to pH2 with 2N HCl and extracted with diethyl ether (2×80 ml). The combined extracts were washed with saturated aqueous potassium bicarbonate solution (50 ml) and water (50 ml), dried over anhydrous sodium sulphate and evaporated under vacuum to give a crude product (14.9 g). This material was further purified by chromatography on silica (Kieselgel 60, 230–240 mesh, Merck) (300 g) eluting with dichloromethane - ethyl acetate 9:1. Appropriate fractions were combined and evaporated to dryness to give the title product (8.35 g). The NMR spectrum was fully consistent with the proposed structure.

EXAMPLE 11

5-Oxo-avermectin B1a

Avermectin B1a (2.4 g) was dissolved in diethyl ether (50 ml) and activated manganese dioxide (2.0 g) added. The mixture was stirred at room temperature for 18 hours, filtered and evaporated to dryness under vacuum to yield the title product whose NMR spectrum was fully consistent with the proposed structure.

EXAMPLE 12

5-Oximino-avermectin B1a

5-Oxo-avermectin B1a (800 mg) (Example 11) was dissolved in pyridine (10 ml) and hydroxylamine hydrochloride (800 mg) added. After stirring at room temperature for 1 hour the mixture was poured into an ice (50 g) and water(50 ml) mixture, acidified to pH 4 with concentrated hydrochloric acid and extracted with dichloromethane (3×30 ml). The combined extracts were washed with water (20 ml), dried over anhydrous sodium sulphate and evaporated to dryness under reduced pressure to yield a crude material (1 g). This material was chromatographed on silica (Kieselgel 60, 230–400 mesh, Merck) (10 g) eluting with dichloromethane: ethyl acetate 2:1 and finally purified by high pressure liquid chromatography using a Dynamax (trade mark) column (41.4×250 mm, 8 $\mu$m ODS-silica, Rainin) eluting with methanol:water 85:15 at 70 ml per minute. Appropriate fractions were combined and evaporated under vacuum to give the title compound (290 mg). Mass and NMR spectra were fully consistent with the proposed structure.

EXAMPLE 13

5-Oximino-avermectin B1a monosaccharide 5-oximino-avermectin B1a (50 mg) (Example 12 ) was dissolved in a mixture of isopropanol (1 ml) and sulphuric acid (10 $\mu$l) and stirred at room temperature under a nitrogen atmosphere for 48 hours. A saturated aqueous solution of sodium bicarbonate (1 ml) was then added and the product extracted with ethylacetate (2×5 ml). The combined extracts were dried over anhydrous magnesium sulphate and concentrated under vacuum. The resulting crude product (25 mg) was purified using high pressure liquid chromatography on an Ultrasphere (trade mark) column (24×250 mm, 5 microns, ODS-silica, Beckman) eluting with methanol: water 85:15 at 20 ml per minute. Appropriate fractions were combined, to give the title product. Mass and NMR spectra were fully consistent with the proposed structure.

EXAMPLE 14

4'-O-Acetyl-25-cyclohexyl-22,23-dihydroavermectin B1 monosaccharide

5-O-t-Butyldimethylsilyl-25-cyclohexyl-22,23-dihydroavermectin B1 monosaccharide (Example 10) (216 mg) was dissolved in dichloromethane (25 ml) containing pyridine (400 mg). Acetic anhydride (255 mg) in dichloromethane (5 ml) was added slowly to this solution at room temperature and the reaction mixture was allowed to stand for 72 hr. The solution was poured into water (20 ml), the organic layer was washed with aqueous citric acid solution (20%, 2×10 ml), saturated aqueous potassium bicarbonate solution (2×10 ml), dried over anhydrous sodium sulphate and evaporated to dryness under vacuum. This crude product was chromatographed on silica (25 g) eluting with dichloromethane - ethyl acetate 9:1. Appropriate fractions were combined and evaporated under vacuum to give 4'-O-acetyl-5-O-t-butyldimethylsilyl-25-cyclohexyl-22,23-dihydroavermectin B1 monosaccharide which was dissolved in methanol (20 ml) containing p-toluenesulphonic acid (230 mg). After stirring at room temperature for 1 hr, saturated aqueous potassium bicarbonate solution (5 ml) was added and the product extracted with diethyl ether (2×10 ml). The combined organic extracts were dried over anhydrous sodium sulphate and evaporated to dryness under vacuum to give the title product as a white powder (139 mg) whose NMR spectra were fully consistent with the proposed structure. This material was used in the following example without further purification.

EXAMPLE 15

4-O-Acetyl-5-oximino-25-cyclohexyl-22,23-dihydroavermectin B1 monosaccharide 4'-O-Acetyl-25-cyclohexyl-22,23-dihydroavermectin B1 monosaccharide (139 mg) (Example 14) was oxidised to the 5-oxo-derivative using activated manganese dioxide (140 mg) in diethyl ether (20 ml) according to the method described in example 2. To a solution of this 4'-O-acetyl-5-oxo-25-cyclohexyl-22,23-dihydroavermectin B1 monosaccharide in a mixture of methanol - dioxan 1:1 (20 ml) was added a solution of hydroxylamine hydrochloride (176 mg) dissolved in water (5 ml). This mixture was stirred at 40° C. for 3 hr before quenching with the addition of solid potassium bicarbonate (200 mg) and diethyl ether (50 ml). The organic extract was washed with saturated aqueous sodium chloride solution (10 ml), dried over anhydrous sodium sulphate and evaporated to dryness under vacuum to give the crude product. This material was then purified by chromatography on silica (Kieselgel 60, 230–400 mesh, Merck) (log) eluting with dichloromethane - ethyl acetate 4:1. Appropriate fractions were combined and evaporated to give the desired compound which was further purified using high pressure liquid chromatography on a Ultrasphere (trade mark) column (10×250 mm, 5 $\mu$m, ODS-silica, Beckman) eluting with acetonitrile:methanol:water 71:14:15 at 5 ml per minute. Appropriate fractions were combined and evaporated to dryness to yield the title product as a white solid (46 mg). Mass and NMR spectra were fully consisted with the proposed structure.

EXAMPLE 16

4'-oxo-5-O-Butyldimethylsilyl-25-cyclohexyl-22,23-dihydroavermectin B1 monosaccharide 5-O-Butyldimethylsilyl-25-cyclohexyl-22,23-dihydroavermectin B1 monosaccharide (Example 10) (1.4 g) was dissolved in dichloromethane (300 ml) at room temperature together with N-methyl morpholine-N-oxide (3.14 g) and tetra-n-propylammonium perruthenate (233 mg). Powdered molecular sieve, 4A (187 mg) was added and the mixture stirred. After 1 hour aqueous sodium sulphite solution, (50 ml, 5%) was added and the separated organic phase washed with a second portion of aqueous sodium sulphite (50ml, 5%), water (2×50ml), saturated aqueous sodium chloride solution (2×50ml) and dried over anhydrous sodium sulphate. Evaporation of the solvent under vacuum followed by chromatography on silica (Kieselgel 60, 230–400 mesh, Merck) eluting with dichloromethane-ethyl acetate 9:1 and combination and evaporation of appropriate fractions, gave the title Droduct as a solid (857 mg). The NMR spectra were fully consistent with the proposed structure.

EXAMPLE 17

4'-epi-5-O-t-Butyldimethylsilyl-25-cyclohexyvl-22,23-dihydroavermectin B1 monosaccharide 4'-oxo-5-O-t-Butyldimethylsilyl-25-cyclohexyl-22,23-dihydroavermectin B1 monosaccharide (200 mg) was dissolved in methanol (10 ml) at 0° C. and sodium borohydride (20 mg) added portionwise with stirring. After 15 minutes the mixture was poured into water, extracted with diethyl ether (2×30ml) and the combined organic extract washed with water (20 ml), saturated aqueous sodium chloride solution (20 ml) and dried over anhydrous sodium sulphate. Evaporation of the solvent under vacuum afforded the title Droduct as a white solid, 141 mg. Mass and NMR spectra were fully consistent with the proposed structure.

EXAMPLE 18

4'-epi-25-Cyclohexyl-22,23-dihydroavermectin B1 monosaccharide

4'-epi-5-O-t-Butyldimethylsilyl-22,23-dihydroavermectin B1 monosaccharide 141 mg, was dissolved in methanol (20 ml) containing p-toluenesulphonic acid (200 mg). After 18 hours the reaction mixture was basified by adding saturated aqueous potassium bicarbonate solution (20 ml) and extracted with diethyl ether (2×50ml). The combined extracts were washed with water (20 ml), saturated aqueous sodium chloride solution (20 ml), dried over anhydrous sodium sulphate and evaporated under vacuum to yield the crude product. Chromatography of this material on silica (Kieselgel 60, 230–400 mesh, Merck) (2g) eluting with dichloromethane-ethyl acetate 4:1 and combination and evaporation under vacuum of appropriate fractions, afforded the title product (100 mg). Mass and NMR spectra were fully consistent with the proposed structure.

EXAMPLE 19

4'-epi-5-Oxo-25-cyclohexyl-22,23-dihydroavermectin B1 monosaccharide

4'-epi-25-Cyclohexyl-22,23-dihydroavermectin B1 monosaccharide (196 mg) was oxidised with activated manganese dioxide according to the procedure described in Example 2. The NMR spectrum of the product (160 mg) was fully consistent with the proposed structure.

EXAMPLE 20

4'-epi-5-Oximino-25-cyclohexyl-22,23-dihydroavermectin B1 monosaccharide

4'-epi-5-Oxo-25-cyclohexyl-22,23-dihydroavermectin B1 monosaccharide (160 mg) was treated with hydroxylamine hydrochloride (150 mg) in a methanol-dioxan-water mixture 1:1:0.5 (25 ml) and the product extracted, according to the procedure described in Example 15. Purification was achieved using high pressure liquid chromatography on a Ultrasphere (trade mark) column (10×250 mm, 5$\mu$, ODS-silica, Beckmann) eluting with acetonitrile-methanol-water, 61:14:25 at 4 ml per minute. Appropriate fractions were combined and evaporated under vacuum to give the title product as a solid (25 mg). Mass and NMR spectra were fully consistent with the proposed structure.

EXAMPLE 21

4a-Hydroxy-25-cyclohexyl-22,23-dihydroavermectin B1 monosaccharide

To a solution of 25-cyclohexyl-22,23-dihydroavermectin B1 monosaccharide (Example 4) (5g) in dichloromethane (150 ml) was added a solution of selenium dioxide (370 mg) and t-butylhydroperoxide (70%, 3.7 ml) in dichloromethane (50 ml) and the whole stirred at room temperature for 48 hours. A further solution containing selenium dioxide (370 mg) and t-butylhydroperoxide (70%, 3.7 ml) in dichloromethane (50 ml) was added and stirring continued for 24 hours. After addition of water (20 ml) the reaction mixture was extracted with dichloromethane (2×25 ml) and the combined extracts washed with 10% aqueous sodium bicarbonate solution (20 ml), and water (20 ml), dried over anhydrous sodium sulphate and evaporated under vacuum to yield the crude product as a yellow foam, 4.5 g. This material was further purified by chromatography over silica (Kieselgel 60, 230–400 mesh, Merck) (120 g) eluting with dichloromethane-methanol 97:3, taking 200 ml fractions. Material eluting in fractions 21–24 was combined and evaporated under vacuum to yield the title comDound as a white powder. Mass and NMR spectra were fully consistent with the proposed structure.

EXAMPLE 22

4a-t-Butyldimethylsilyloxy-25-cyclohexyl-22,23-dihydroavermectin B1 monosaccharide 4a-Hydroxy-25-cyclohexyl-22,23-dihydroavermectin B1 monosaccharide (1.26 g), triethylamine (0.2 ml) and 4-dimethylaminopyridine (26 mg) were dissolved by stirring in dry dichloromethane (120 ml) and t-butyldimethylsilyl chloride (0.32 g) added portionwise. The whole was stirred under a nitrogen atmosphere for 18 hours after which further quantities of triethylamine (0.4 ml), 4-dimethylaminopyridine (252 mg) and t-butyldimethylsilyl chloride (0.64 g) were added and stirring continued for 3 hours. An aqueous solution of sodium bicarbonate (10%, 100 ml) was added to the reaction and the organic layer separated, washed with water (100 ml), dried over anhydrous sodium sulphate and evaporated under vacuum to give the crude product. This material was purified by chromatography on silica (Kieselgel 60, 230–400 mesh, Merck)

(120 g) eluting with dichloromethane-methanol, 98:2 collecting 130 ml fractions. Material eluting in fractions 12–14 were combined and evaporated under vacuum to yield the title compound as a white solid, (1.1 g). Mass and NMR spectra were fully consistent with the proposed structure.

EXAMPLE 23

4a-t-Butyldimethylsilyloxy-5-oxo-25-cyclohexyl-22,23-dihydroavermectin B1 monosaccharide 4a-t-Butyldimethylsilyloxy-25-cyclohexyl-22,23-dihydroavermectin B1 monosaccharide (1.1 g) was oxidised with activated manganese dioxide (1 g) in ether (10 ml) according to the method described in Example 2 to give the title compound (0.9 g) whose NMR spectrum was fully consistent with the proposed structure.

EXAMPLE 24

4a-Hydroxy-5-oximino-25-cyclohexyl-22,23-dihydroavermectin B1 monosaccharide 4a-t-Butyldimethylsilyloxy-5-oxo-25-cyclohexyl-22,23-dihydroavermectin B1 monosaccharide (0.9 g) was dissolved in a methanol-dioxan (1:1 mixture , 36 ml) and hydroxylamine hydrochloride (0.9 g) dissolved in water (18 ml) added. This reaction mixture was stirred and heated at 40° C. for 1 hour then concentrated to approximately 20 ml by evaporation under vacuum and the product extracted with diethyl ether (2×50 ml). The combined extracts were washed with aqueous sodium bicarbonate solution (10%, 30 ml), water (50 ml), dried over anhydrous sodium sulphate and evaporated under vacuum to yield the crude product. This material was chromatographed on silica (Kieselgel, 60, 230–400 mesh, Merck) (50 g) eluting with dichloromethane-methanol gradient 99:1 to 96:4 collecting 50 ml fractions over 1.5 hours. Fractions 50–54 were combined and evaporated under vacuum to give material which was further purified by high pressure liquid chromatography on an Dynamax (trade mark) column (24×250 mm, 5 µm, ODS-silica, Rainin) eluting with methanol-water 80:20 at 20 ml per minute. Appropriate fractions were combined and evaporated under vacuum to yield the title compound as a white powder. Mass and NMR spectra were fully consistent with the proposed structure.

EXAMPLE 25

4'-Methyl-5-O-t-butyldimethylsilyl-25-cyclohexyl-22,23-dihydroavermectin B1 monosaccharide 4'-Oxo-5-O-t-butyldimethylsilyl-25-cyclohexyl-22,23-dihydroavermectin B1-monosaccharide (Example 16) (174 mg) was dissolved in dry ether (15ml) and cooled to 0° C. under a nitrogen atmosphere. To this solution was added a solution of methyl magnesium bromide (115 µl, 3M in diethyl ether) dropwise, and stirring continued for a further 1 hour. After quenching, by adding an aqueous solution of ammonium chloride, (10 ml, 10%), the organic layer was separated, washed with water (2×10 ml), dried over anhydrous sodium sulphate and evaporated under vacuum to give the crude product. This material was chromatographed on silica (Kieselgel 60, 230–400 mesh, Merck) (20 g) eluting with dichloromethane-ethyl acetate 9:1. Combining appropriate fractions, and evaporation under vacuum afforded the product which was used without further purification.

EXAMPLE 26

4'-Methyl-25-cyclohexyl-22,.23-dihvdroavermectin B1 monosaccharide

4'-Methyl-5-O-t-butyldimethylsilyl-25-cyclohexyl-22,23-dihydroavermectin B1 monosaccharide (74 mg) (Example 25) was dissolved in methanol (20 ml) containing p-toluenesulphonic acid (36 mg) and stirred at ambient temperature for 2 hours. After this time solid potassium bicarbonate (50 mg) was added and the mixture diluted with water (20 ml) and extracted with diethyl ether (2×20 ml). The combined extracts were washed with water (20 ml), saturated aqueous sodium chloride solution (10 ml), dried over anhydrous sodium sulphate and evaporated under vacuum to yield a crude product. This material was chromatographed on silica (Kieselgel 60, 230–400 mesh, Merck) (10 g) eluting with dichloromethane-ethyl acetate 4:1. Appropriate fractions were combined and evaporated under vacuum to give the product which was further purified by preparative high pressure liquid chromatography on an Ultrasphere (trade mark) column (10×250 mm, 5 µm, ODS-silica, Beckmann) eluting with methanol-water 85:15 at 5 ml per minute. Appropriate fractions were combined and evaporated under vacuum to yield the title product as a white powder. Mass and NMR spectra were fully consistent with the proposed structure.

EXAMPLE 27

4'-Methyl-5-oxo-25-cyclohexyl-22,23-dihydroavermectin B1 monosaccharide

4'-Methyl-25-cyclohexyl-22,23-dihydroavermectin B1 monosaccharide (255 mg) was oxidised with activated manganese dioxide (250 mg) in diethyl ether (50 ml) according to the procedure described in Example 2 to give the title compound (208 mg) whose NMR spectrum was fully consistent with the proposed structure.

EXAMPLE 28

4-Methyl-5-oximino-25-cyclohexyl-22,23-dihydroavermectin B1 monosaccharide

To a solution of 4'-methyl-5-oxo-25-cyclohexyl-22,23-dihydroavermectin B1 monosaccharide (208 mg) in a mixture of methanol:dioxan 1:1 (40 ml) was added a solution of hydroxylamine hydrochloride (416 mg) dissolved in water (10 ml). This mixture was stirred at room temperature and a further amount of hydroxylamine hydrochloride (208 mg) was added after 3 hr and stirring continued at 50° C. for 5 hr before quenching with the addition of saturated aqueous potassium bicarbonate solution (20 ml) and diethyl ether (50 ml). The organic extract was washed sequentially with water (20 ml) and saturated aqueous sodium chloride solution (20 ml), dried over anhydrous sodium sulphate and evaporated to dryness under vacuum to give the crude product. This material was then chromatographed on silica (Kieselgel 60, 230–400 mesh, Merck) (10 g) eluting with dichloromethane:ethyl acetate 4:1. Appropriate fractions were combined and evaporated to give the desired compound which was further purified using high pressure liquid chromatography on a Dynamax (trade mark) column (10×250mm, 5 µm, Ultrasphere (trade mark) ODS-silica, Beckman) eluting with acetonitrile:methanol:water 63:12:25 at 5 ml per minute. Appropriate fractions were combined and evaporated to dryness to yield the title product as a white solid (63 mg). Mass and NMR spectra were fully consisted with the proposed structure.

EXAMPLE 29

5-O-t-Butyldimethylsilyloximino-22,23-dihyro-25-cyclohexylavermectin B1 monosaccharide Method 1. 5-Oximino-22,23-dihydro-25-cyclohexylavermectin B1 monosaccharide (5.93 g)

(Example 5), t-butyldimethylsilyl chloride (2.11 g) and imidazole (1.9 g) were dissolved in dichloromethane (20 ml) and the mixture stirred at room temperature for 1 hr. Further amounts of t-butyldimethylsilyl chloride (2.11 g) and imidazole (1.9 g) were then added and the reaction mixture stirred at 40° C. for another 0.5 hr. The mixture was washed with water (2×20 ml), saturated aqueous potassium bicarbonate solution (10 ml), dried over anhydrous sodium sulphate and evaporated to dryness under vacuum to give the crude product. Purification was achieved by chromatography on silica (Kieselgel 60, 230–400 mesh, Merck) (250 g) eluting with dichloromethane: ethyl acetate 9:1. Appropriate fractions were combined and evaporated to give the title compound as a white powder (4.0 g).

Method 2. 22,23-Dihydro-25-cyclohexylavermectin B1 monosaccharide (Example 4) was oxidized to the 5-oxo derivative using manganese dioxide in anhydrous diethyl ether according to a procedure of Example 2. The 5-oxo-22,23-dihydro-25-cyclohexylavermectin B1 monosaccharide (5.0 g) was dissolved in dichloromethane (200 ml) and O-(t-butyldimethylsilyl)-hydroxylamine (2.5 g) and glacial acetic acid (10 ml) were added. The reaction mixture was stirred at room temperature for 18 hrs and then washed with water (50 ml), saturated aqueous potassium bicarbonate solution (50 ml), dried over anhydrous sodium sulphate and evaporated to dryness under vacuum to give the crude product. Final purification was achieved by chromatography over silica (Kieselgel 60, 230–400 mesh, Merck) (250 g) eluting with a gradient of hexane:diethyl ether 2:1 changing to 1:1. Appropriate fractions were combined and evaporated to give the title compound as a white powder (3.9 g).

The NMR spectrum of the products from the two methods was fully consistent with the proposed structure.

EXAMPLE 30

4'-Acetylamino-4'-deoxy-5-oximino-22,23-dihydro-25-cyclohexylavermectin B1 monosaccharide To a solution of 5-O-t-Butyldimethylsilyloximino-22,23-dihydro-25-cyclohexylavermectin B1 monosaccharide (620 mg) (Example 29) in dichloromethane (40 ml) were added tetrapropylammonium perruthenate (100 mg) and N-methylmorpholine N-oxine (600 mg). The reaction mixture was stirred at room temperature for 1 hour and then applied to the top of a silica chromatography column (Kieselgel 60, 230–400 mesh, Merck) (30 g). Following elution with dichloromethane, appropriate fractions were combined and evaporated to give the 4'-oxo-derivative which was used directly in the next step by dissolution in methanol (10 ml), adding ammonium acetate (1.0 g) followed by sodium cyanoborohydride portionwise until TLC indicated complete reduction. The solvent was then removed by evaporation under reduced pressure, the residue taken up in dichloromethane (10 ml) and triethylamine (5001) and acetic anhydride (2001) were added. After 1 hr TLC indicated that the reaction was complete. The mixture was evaporated under reduced pressure, the residue taken up in methanol (10 ml) and solid p-toluenesulphonic acid added until the solution pH was 3.0. After 1 hr TLC indicated that deprotection was complete and the reaction mixture was poured into a mixture of aqueous sodium bicarbonate solution and ether 1:1 (20 ml). The organic layer was separated, dried over anhydrous sodium sulphate and evaporated to dryness under vacuum to give the crude product. Purification was achieved by high pressure liquid chromatography on an Dynamax (trade mark) column (24×250 mm, 5 µm, ODS-silica, Rainin) eluting with methanol-water 85:15 at 20 ml per minute. Appropriate fractions were combined and evaporated under vacuum to give the product which was further purified by high pressure liquid chromatography on an Dynamax (trade mark) column (24×250mm, 5 µm, ODS-silica, Rainin) eluting with methanol-water 82:18 at 20 ml per minute. Appropriate fractions were combined and evaporated under vacuum to yield the title compound as a white powder (50 mg). Mass and NMR spectra were fully consistent with the proposed structure.

EXAMPLE 31

5-Oximino-25-cyclohexylavermectin B2

25-Cyclohexylavermectin B2 (50 g) was oxidised to its 5-oxo-derivative with activated manganese dioxide (2×50 g) in diethyl ether (500 ml) according to the method described in Example 2. Further reaction with hydroxylamine hydrochloride (53 g) in an aqueous methanol-dioxan-water mixture (1:1:1) (900 ml) was carried out according to the procedure described in Example 28. The title product was isolated from the reaction by pouring into water (500 ml) and extracting with diethyl ether (3×500 ml). The combined organic extracts were dried over anhydrous magnesium sulphate and evaporated to dryness under vacuum to give the product (53 g) which was used directly in the next example without further purification.

EXAMPLE 32

5-Oximino-23-oxo-25-cyclohexylavermectin B2 monosaccharide

A mixture of 5-Oximino-25-cyclohexylavermectin B2 (500 mg) and pyridinium dichromate (1.87 g) in dimethylformamide (25 ml) was stirred at room temperature under a nitrogen atmosphere for 18 hrs. The reaction mixture was then poured into an ice (25 g) and (50 ml) mixture and extracted with diethyl ether (2×50ml). The combined ether extract was washed with 2N hydrochloric acid (20 ml), water (50 ml), dried over anhydrous magnesium sulphate and evaporated to dryness under vacuum to give a residue (350 mg) which was dissolved in isopropanol (25 ml) containing 1% sulphuric acid v/v. After stirring this reaction mixture for 18 hrs under a nitrogen atmosphere it was poured into an ice-water mixture (50 ml) and the product extracted with dichloromethane (2×30 ml). The combined organic extracts were dried over anhydrous magnesium sulphate and evaporated to dryness under vacuum to give the crude product (300 mg) which was purified by high pressure liquid chromatography on a Zorbax column (21.2×250 mm, 8 µm, ODS-silica, Rainin) eluting with methanol-water 78:22 at 9 ml per minute. Appropriate fractions were combined and evaporated under vacuum to yield the title compound as a white powder. Mass and NMR spectra were fully consistent with the proposed structure.

EXAMPLE 33

5-Oximino-23-methoximino-25-cyclohexylavermectin B2 monosaccharide

To a solution of 5-oximino-23-oxo-25-cyclohexylavermectin B2 monosaccharide (300 mg) (Example 32) in dioxan (150 ml) containing sodium acetate (320 mg) and methoxylamine hydrochloride (370 mg) was added glacial acetic acid (10 ml). The reaction was stirred at room temperature for 18 hrs then poured into water (200 ml)

and extracted with dichloromethane (2×200 ml). The combined extracts were washed with saturated aqueous sodium bicarbonate solution (2×100 ml) and water (100 ml), dried over anhydrous magnesium sulphate and evaporated to dryness under vacuum to give the crude product which was chromatographed on silica (Kieselgel 60, 230–400 mesh, Merck) (10 g) eluting with a gradient of hexane:diethyl ether 1:1 changing to 0:1. Appropriate fractions were combined and evaporated to give the product (98 mg) which was further purified by high pressure liquid chromatography on a Zorbax column (21.2×250 mm, 8 μm, ODS-silica, Rainin) eluting with methanol-water 82:18 at 9 ml per minute. Appropriate fractions were combined and evaporated under vacuum to yield the title compound as a white powder (60 mg). Mass and NMR spectra were fully consistent with the proposed structure.

EXAMPLE 34

4'-O-Succinoyl-5-O-t-butyldimethylsilyloximino-25-cyclohexyl-22,23-dihydroavermectin B1 monosaccharide To a solution of 5-O-t-butyldimethylsilyloximino-22,23-dihydro-25-cyclohexyl-avermectin B1 monosaccharide (Example 29) (530 mg), diisopropylethylamine (770 mg) and 4-dimethylaminopyridine (73 mg) in dichloromethane (50 ml) was added succinic anhydride (3.6 g). The resulting suspension was sonicated for 10 min and stirred at room temperature for 18 hr then washed with water (2×10 ml), dried over anhydrous sodium sulphate and evaporated to dryness under vacuum to give the crude product which was chromatographed on silica (Kieselgel 60, 230–400 mesh, Merck) (20 g) eluting with a gradient of dichloromethane-ethyl acetate 9:1 changing to 4:1. Appropriate fractions were combined and evaporated to give a solid which was slurried with dichloromethane (20 ml), filtered and the filtrate evaporated to dryness under vacuum to give the crude product which was further purified by high pressure liquid chromatography on a Dynamax (trade mark) column (41.4×250 mm, 8 μm, ODS-silica, Rainin) eluting at 9 ml per minute with a methanol-water 90:10 mixture changing to 95:5 after 40 mins. Appropriate fractions were combined and evaporated under vacuum to yield the title compound as a white powder (407 mg). Mass and NMR spectra were fully consistent with the proposed structure.

EXAMPLE 35

4'-O-Succinoyl-5-oximino-25-cyclohexyl-22,23-dihydroavermectin B1 monosaccharide A solution of 4'-O-succinoyl-5-O-t-butyldimethylsilyloximino-22,23-dihydro -25-cyclohexyl-avermectin B1 monosaccharide (Example 34) (50mg), and p-toluenesulphonic acid (50 mg) in a dioxan-water mixture 10:1 (11 ml) was stirred at room temperature for 2 hr. This reaction mixture was then quenched by the addition of saturated aqueous potassium bicarbonate solution (5 ml) and water (10 ml) and the product extracted with diethyl ether (3×20 ml). The combined organic extracts were washed with water (3×10 ml), saturated aqueous sodium chloride solution (5 ml), dried over anhydrous sodium sulphate and evaporated to dryness under vacuum to give the crude product which was chromatographed on silica (Kieselgel 60, 230–400 mesh, Merck) (0.5 g) eluting with ethyl acetate. Appropriate fractions were combined and evaporated to give a solid (46 mg) which was further purified by high pressure liquid chromatography on a Utrasphere column (10×250 mm, 5 μm, ODS-silica, Beckman) eluting at 5 ml per minute with a methanol-water 80:20 mixture changing to 85:15 after 20 mins and to 90:10 after 40 mins. Appropriate fractions were combined and evaporated under vacuum to yield the potassium salt of the title compound as a white powder (32 mg). This compound was dissolved in diethyl ether (10 ml), washed with an aqueous citric acid solution (20% w/v, 5 ml), dried over anhydrous sodium sulphate and evaporated to dryness under vacuum to give the title compound as a white powder (25 mg). Mass and NMR spectra were fully consistent with the proposed structure.

EXAMPLE 36

4'-O-(3-Methoxycarbonypropanoyl)-5-oximino-25-cyclohexyl -22,23-dihydroavermectin 1 monosaccharide A solution of 4'-O-succinoyl-5-O-t-butyldimethylsilyloximino-22,23-dihydro -25-cyclohexyl-avermectin B1 monosaccharide (Example 34) (50 mg), and p-toluenesulphonic acid (50 mg) in methanol (10 ml) was stirred at room temperature for 1 hr. This reaction mixture was then quenched by the addition of saturated aqueous potassium bicarbonate solution (2 ml) and water (10 ml) and the product extracted with diethyl ether (3×10 ml). The combined organic extracts were washed with water (3×5 ml), saturated aqueous sodium chloride solution (2×5 ml), dried over anhydrous sodium sulphate and evaporated to dryness under vacuum to give the crude product which was chromatographed on silica (Kieselgel 60, 230–400 mesh, Merck) (1 g) eluting with dichloromethane-ethyl acetate 9:1. Appropriate fractions were combined and evaporated to give the title compound as a white powder. Mass and NMR spectra were fully consistent with the proposed structure.

EXAMPLE 37

4'-O-3-( 4-Methylpiperazin-1-yl) carbonylpropanoyl)-5-oximino-25-cyclohexyl-22,23-dihydroavermectin B1 monosaccharide To a solution of 4'-0-succinoyl-5-O-t-butyldimethylsilyloximino-22,23-dihydro-25-cyclohexyl-avermectin B1 monosaccharide (Example 34) (100 mg), 1-hydroxybenzotriazole (15 mg) and 1-(3-dimethylaminopropyl)-3-ethylcarbodiimide (24 mg) in dry N,N-dimethylformamide (5 ml) was added and N-methylpiperazine (11 mg) and the mixture stirred at room temperature for 18 hr. After pouring into water (20 ml) the product was extracted with diethyl ether (3×10 ml). The combined extracts were washed with water (3×5 ml), saturated aqueous sodium chloride solution (2×5 ml), dried over anhydrous sodium sulphate and evaporated to dryness under vacuum to give a material which was chromatographed on silica (Kieselgel 60, 230–400 mesh, Merck) (log) eluting with dichloromethane-methanol 95:5. Appropriate fractions were combined and evaporated to give a material (85 mg) which was dissolved in methanol (10 ml) containing p-toluenesulphonic acid (85 mg) and the whole stirred at room temperature for 1 hr. This reaction mixture was quenched by adding saturated aqueous potassium bicarbonate (5 ml) and water (20 ml) and the product extracted with diethyl ether (3×10 ml). The combined organic extracts were washed with water (3×5 ml), saturated aqueous sodium chloride solution (2×5 ml), dried over anhydrous sodium sulphate and evaporated to dryness under vacuum to give the crude product which was chromatographed on silica (Kieselgel 60, 230–400 mesh, Merck) (10 g) eluting with dichloromethane-methanol 95:5. Appropriate fractions were combined and evaporated to give the title compound as a white powder (52 mg). Mass and NMR spectra were fully consistent with the proposed structure.

EXAMPLE 38

4'-O- (3-(Pyrid-4-ylamino)carbonylpropanoyl) -5-oximino-25-cyclohexyl-22,23-dihydroavermectin B1 monosaccharide To a solution of 4'-O-succinoyl-5-O-t-butyldimethylsilyloximino-22,23-dihydro -25-cyclohexyl-avermectin B1 monosaccharide (Example 34) (100 mg), 1-hydroxybenzotriazole (30 mg), 1-(3-dimethylaminopropyl)-3-ethylcarbodiimide (48 mg) and diisopropylethylamine (39 mg) in dry N,N-dimethylformamide (5 ml) was added 4-aminopyridine (21 mg) and the mixture stirred at room temperature for 18 hr. After pouring into ethyl acetate (20 ml) the resulting solution was washed with water (3×10 ml), saturated aqueous sodium chloride solution (2×5 ml), dried over anhydrous sodium sulphate and evaporated to dryness under vacuum to give a material (90 mg) which was dissolved in methanol (10 ml) containing p-toluenesulphonic acid (20 mg) and the whole stirred at room temperature for 1 hr. This reaction mixture was quenched by adding saturated aqueous potassium bicarbonate (5 ml) and water (20 ml) and the product extracted with diethyl ether (3×10 ml). The combined organic extracts were washed with water (3×5 ml), saturated aqueous sodium chloride solution (2×5 ml), dried over anhydrous sodium sulphate and evaporated to dryness under vacuum to give the crude product which was chromatographed on silica (Kieselgel 60, 230–400 mesh, Merck) (5 g) eluting with ethyl acetate. Appropriate fractions were combined and evaporated to dryness under vacuum to give the title compound as a white powder (29 mg). Mass and NMR spectra were fully consistent with the proposed structure.

EXAMPLE 39

4'-O-(N,N'-bis-(9-Fluorenylmethoxycarbonyl) lysinyl)-5-O-t-butyldimethylsilyloximino-25-cyclohexyl-22,23-dihydroavermectin B1 monosaccharide To a solution of N,N'-bis-(9-fluorenylmethoxycarbonyl) lysine (1.32 g) in dichloromethane (250 ml) was added dicyclohexylcarbodiimide (230 mg) and the mixture stirred at room temperature for 1 hr. The resulting suspension was then sonicated for 0.5 hr then filtered through a layer of Hyflo (trade mark) and the filtrate concentrated under reduced pressure to a volume of approximately 100 ml to give a solution of the desired N,N'-bis-(9-fluorenylmethoxycarbonyl)lysine anhydride. To this solution was added 5-O-t-butyldimethylsilyloximino-22,23-dihydro-25-cyclohexyl-avermectin B1 monosaccharide (Example 29) (670 mg), diisopropylethylamine (294 mg) and 4-dimethylaminopyridine (185 mg). The reaction mixture was stirred at room temperature for 90 hrs then concentrated to dryness under reduced pressure to give a residue which was chromatographed on silica (Kieselgel 60, 230–400 mesh, Merck) (200 g) eluting with dichloromethane changing to dichloromethane-ethyl acetate 9:1 after 11 had been collected. Appropriate fractions were combined and evaporated to dryness under vacuum to give the title compound as a white powder (850 mg). The NMR spectrum was fully consistent with the proposed structure.

EXAMPLE 40

4'-O-(N,N'-bis-(9-Fluorenylmethoxycarbonyl) lysinyl)-5-oximino-25-cyclohexyl-22,23-dihydroavermectin B1 monosaccharide 4'-O-(N,N'-bis-(9-fluorenylmethoxycarbonyl)lysinyl)-5-O-t-butyldimethylsilyloximino-25-cyclohexyl-22,23-dihydroavermectin B1 monosaccharide (850 mg) (Example 39) was dissolved in methanol (20 ml) containing p-toluenesulphonic acid (20 mg) and the whole stirred at room temperature for 2 hrs. This reaction mixture was quenched by adding saturated aqueous potassium bicarbonate (5 ml) and water (20 ml) and the product extracted with diethyl ether (3×10 ml). The combined organic extracts were washed with water (3×5 ml), saturated aqueous sodium chloride solution (2×5 ml), dried over anhydrous sodium sulphate and evaporated to dryness under vacuum to give the crude product which was chromatographed on silica (Kieselgel 60, 230–400 mesh, Merck) (25 g) eluting with dichloromethane-ethyl acetate 9:1 changing to 4:1 after 200 ml of eluate had been collected. Appropriate fractions were combined and evaporated to dryness under vacuum to give the title compound as a white powder (274 mg). The NMR spectrum was fully consistent with the proposed structure.

EXAMPLE 41

4'-O-Lysinyl-5-oximino-25-cyclohexyl-22,23-dihydroavermectin B1 monosaccharide

4'-O-(N,N'-bis-(9-fluorenylmethoxycarbonyl)lysinyl)-5-oximino-25-cyclohexyl-22,23-dihydroavermectin B1 monosaccharide (274 mg) (Example 40) was dissolved in acetonitrile (30 ml) containing piperidine (150 mg) and the mixture stirred at room temperature for 8 hrs. This was concentrated to dryness under vacuum to give the crude product which was chromatographed on silica (Kieselgel 60, 230–400 mesh, Merck) (25 g) eluting with dichloromethane-methanol -0.880 ammonia solution 80:20:1. Appropriate fractions were combined and evaporated to dryness under vacuum to give the title compound which was freeze dried from t-butanol to yield a white powder (157 mg). Mass and NMR spectra were fully consistent with the proposed structure.

EXAMPLE 42

5-(Trimethylacetyloximino)-25-cyclohexyl-22-23-dihydroavermectin B1 monosaccharide To a stirred solution of 5-oximino-25-cyclohexyl-22,23-dihydroavermectin B1 monosaccharide (Example 5) (50 mg) in dichloromethane (2 ml) at room temperature was added triethylamine (721) followed by trimethylacetyl chloride (801). After leaving to stand for 18 hrs an aqueous citric acid solution (10% w/v, 2 ml) was added and the organic layer separated, washed with saturated aqueous sodium chloride solution (2 ml), dried over anhydrous sodium sulphate and evaporated to dryness under vacuum to give the crude product which was chromatographed on silica (Kieselgel 60, 230–400 mesh, Merck) (5 g) eluting with diethyl ether. Appropriatefractions were combined and evaporated to dryness under vacuum to give a material (53 mg) which was further purified by high pressure liquid chromatography on a Dynamax (trade mark) column (21.2× 250 mm, 5 μm, ODS-silica, Rainin) eluting at 20 ml per minute with a methanol-water 95:5 mixture. Appropriate fractions were combined and evaporated under vacuum to yield the title compound as a white powder (18 mg). Mass and NMR spectra were fully consistent with the proposed structure.

EXAMPLE 43

5-(Benzoyloximino)-25-cyclohexyl-22,23-dihydroavermectin B1 monosaccharide 5-oximino-25-cyclohexyl-22,23-dihydroavermectin B1 monosaccharide (Example 5) (70 mg) in dichloromethane (30 ml) was reacted with triethylamine (501) and benzoyl chloride (1001) and the desired product extracted in a manner identical to that described in Example 42. Purification was achieved by high pressure liquid chromatography on a Dynamax (trade mark) column (41.4×250 mm, 8 μm, ODS-silica, Rainin) eluting at 45 ml per minute with a methanol-water 90:10 mixture. Appropriate fractions were combined and evaporated under vacuum to yield the title compound as a white powder (28 mg). Mass and NMR spectra were fully consistent with the proposed structure.

EXAMPLE 44

5-(N-Methylcarbamoyloximino)-25-cyclohexyl-22, 23-dihydroavermectin B1 monosaccharide To a stirred solution of 5-oximino-25-cyclohexyl-22,23-dihydroavermectin B1 monosaccharide (Example 5) (106 mg) in dichloromethane (10 ml) was added methyl isocyanate (151) and the mixture stirred for 1 hr. A further amount of methyl isocyanate (301) was then added and the reaction stirred for another 72 hrs before adding saturated aqueous sodium chloride solution (10 ml) and ether (30 ml). The organic extract was dried over anhydrous sodium sulphate and evaporated to dryness under vacuum to give the crude product (150 mg) which was purified by high pressure liquid chromatography on a Dynamax (trade mark) column (.41.4× 250 mm, 8 μm, ODS-silica, Rainin) eluting at 45 ml per minute with a methanol-water 91:9 mixture. Appropriate fractions were combined and evaporated under vacuum to yield the title compound as a white powder (80 mg). Mass and NMR spectra were fully consistent with the proposed structure.

EXAMPLE 45

5-(N,N-Dimethylcarbamoyloximino)-25-cyclohexyl-22,23-dihydroavermectin B1 monosaccharide To a stirred solution of 5-oximino-25-cyclohexyl-22,23-dihydroavermectin B1 monosaccharide (Example 5) (50 mg) in dichloromethane (2 ml) at room temperature was added triethylamine (721) and 4-dimethylaminopyridine (1 mg) followed by N,N-dimethylcarbamoyl chloride (581). After 3 hrs further N,N-dimethylcarbamoyl chloride (581) was added and the reaction left to stand for 18 hrs. An aqueous citric acid solution (10% w/v, 2ml) and diethyl ether (20 ml) were then added and the organic layer separated, washed with saturated aqueous sodium chloride solution (5 ml), dried over anhydrous sodium sulphate and evaporated to dryness under vacuum to give the crude product which was purified by high pressure liquid chromatography on a Dynamax (trade mark) column (21.2×250 mm, 5 μm, ODS-silica, Rainin) eluting at 10 ml per minute with a methanol-water 90:10 mixture. Appropriate fractions were combined and evaporated under vacuum to yield the title comDound as a white powder (18 mg). Mass and NMR spectra were fully consistent with the proposed structure.

EXAMPLE 46

5-(4-Methylpiperazinyl-1-carbonyloximino)-25-cyclohexyl-22,23-dihydroavermectin B1 monosaccharide To a stirred solution of N-methylpiperazine (0.65 ml) and triethylamine (1.3 ml) in toluene (25 ml) at 0° C. was added dropwise a solution of phosgene in toluene (20%, 5.1 ml) over a period of 15 min. The reaction was allowed to warm to room temperature, stirred for 3 hr, filtered and concentrated to approximately 10 ml under reduced pressure to give a solution of 1-chlorocarbonyl-4-methylpiperazine which was reacted with 5-oximino-25-cyclohexyl-22,23-dihydroavermectin B1 monosaccharide (Example 5) (300 mg), triethylamine (1101) and 4-dimethylaminopyridine (5 mg) in dichloromethane (10 ml) at room temperature according to the method described in Example 45. Purification of the desired material was achieved by chromatography on silica (Kieselgel 60, 230–400 mesh, Merck) (35 g) eluting with dichloromethane. Appropriate fractions were combined and evaporated to dryness under vacuum to give a material (53 mg) which was further purified by high pressure liquid chromatography on a Dynamax (trade mark) column (21.2×250 mm, 5 μm, ODS-silica, Rainin) eluting at 20 ml per minute with a methanol-water 95:5 mixture. Appropriate fractions were combined and evaporated under vacuum to yield the title compound as a white powder. Mass and NMR spectra were fully consistent with the proposed structure.

EXAMPLE 47

5-(t-Butyloxycarbonyloximino)-25-cyclohexyl-22, 23-dihydroavermectin B1 monosaccharide To a stirred solution of 5-oximino-25-cyclohexyl-22,23-dihydroavermectin B1 monosaccharide (Example 5) (60 mg) and triethylamine (501) in dichloromethane (5 ml) at room temperature was added t-butyloxycarbonyl anhydride (60 mg). After allowing to stand for 48 hrs the reaction was evaporated to dryness under vacuum to give a residue which was dissolved in dichloromethane and chromatographed on silica (Kieselgel 60, 230–400 mesh, Merck) (5 g) eluting with dichloromethane. Appropriate fractions were combined and evaporated to dryness under vacuum to give the title compound as a white powder (45 mg). Mass and NMR spectra were fully consistent with the proposed structure.

EXAMPLE 48

5-(N-(4-Formylphenyl)-carbamoyloximino)-25-cyclohexyl-22, 23-dihydroavermectin B1 monosaccharide 4-Formylphenylisocyanate was prepared according to the method described in J. Med. Chem., 32(10), 2354, (1989) and was reacted with 5-oximino-25-cyclohexyl-22,23-dihydroavermectin B1 monosaccharide (Example 5) (500 mg), in dry dichloromethane (50 ml) at room temperature for 1 hr according to the method described in Example 43. Purification of the desired material was achieved using chromatography over silica (Kieselgel 60, 230–400 mesh, Merck) (125 g) eluting with a gradient of hexane-ether 1:1 changing to 20:80. Appropriate fractions were combined and evaporated to dryness under vacuum to give the title com-Dound as a white powder (300 mg). Mass and NMR spectra were fully consistent with the proposed structure.

EXAMPLE 49

5-(N-(4-(Diethylaminomethyvl)phenyl)-carbamoyloximino)-25-cyclohexyl-22,.23-dihydroavermectin B1 monosaccharide 4-Diethylaminomethylbenzoyl chloride was prepared according to the method described in U.S. Pat. No. 4,623,486 and was reacted with 5-oximino-25-cyclohexyl-22,23-dihydroavermectin B1 monosaccharide (Example 5) (100 mg), in dry dichloromethane (50 ml) containing triethylamine (4501) and 4-dimethylaminopyridine (126 mg) at room temperature for 1 hr according to the method described in Example 45. Purification of the desired material was achieved using chromatography over silica (Kieselgel 60, 230–400 mesh, Merck) (5 g) eluting with a gradient of methanol-dichloromethane 0:100 changing to 10:90. Appropriatefractions were combined and evaporated to dryness under vacuum to give the title compound as a white powder (11 mg). Mass and NMR spectra were fully consistent with the proposed structure.

EXAMPLE 50

5-(N-(4-(4-Methyl-1-piperazinyl-methyl)phenyl)-carbamoyl oximino)-25-cyclohexyl-22.23-dihydroavermectin B1 monosaccharide 4-(4-Methylpiperazin-1-ylmethyl)benzoyl chloride was prepared according to the method described in U.S. Pat. No. 4,623,486 and was reacted with 5-oximino-25-cyclohexyl-22,23-dihydroavermectin B1 monosaccharide (Example 5) in a manner identical to that described in Example 48. The title compound was obtained as a white powder (18 mg). Mass and NMR spectra were fully consistent with the proposed structure.

EXAMPLE 51

5-(N-(3-Pyridylcarbonyvl)-carbamoyloximino)-25-cyclohexyl-22,23-dihydroavermectin B1 monosaccharide To a stirred solution of nicotinamide (4.88 g) in dry 1,2-dichloroethane (500 ml) was added dropwise oxalyl chloride (5.24 ml). The mixture was heated under reflux for 4.5h then cooled, filtered and the resulting solution containing nicotinoyl isocyanate (50 ml) was reacted with 5-oximino-25-cyclohexyl-22,23-dihydroavermectin B1 monosaccharide (Example 5) (500 mg), in dichloromethane (10 ml) at room temperature. After allowing to stand for 18 hr further nicotinoyl isocyanate solution (25 ml) was added and the mixture left at room temperature for a further 18 hr before evaporating to dryness under vacuum to give a residue which was purified by high pressure liquid chromatography on a Dynamax (trade mark) column(41.4×250 mm, 8 μm, ODS-silica, Rainin) eluting at 45 ml per minute with a methanol-acetonitrile-water 20:65:15 mixture. Appropriate fractions were combined and evaporated under vacuum to yield the title compound as a white powder. Mass and NMR spectra were fully consistent with the proposed structure.

EXAMPLE 52

5-(N-(3-Pyridyl)-carbamoyloximino)-25-cyclohexyl-22.23-dihydroavermectin B1 monosaccharide To a solution of nicotinic acid hydrazide dihydrochloride (2 g) in water (10 ml) was added a solution of sodium nitrite (1.6 g) in water (10 ml), keeping the temperature below 20° C. Diethyl ether (50 ml) was then added and the mixture basified by the careful addition of solid sodium bicarbonate. The organic layer was separated, washed with water (20 ml), dried over anhydrous magnesium sulphate and evaporated to dryness under vacuum to give nicotinyl azide (1.1 g) m.pt. 54° C. This azide (1.1 g) was stirred in dry toluene (10 ml) and heated at 100° C. under a nitrogen atmosphere for 8 hr to give a solution containing 3-pyridyl isocyanate. A portion of this solution (1 ml) was reacted with 5-oximino-25-cyclohexyl-22,23-dihydroavermectin B1 monosaccharide (Example 5) (100 mg), in toluene (10 ml) at room temperature for 1 hr before pouring into a diethyl ether-water mixture (1:1, 30 ml). The organic layer was separated, dried over anhydrous magesium sulphate and evaporated to dryness under vacuum to give a residue (130 mg) which was purified by high pressure liquid chromatography on a Dynamax (trade mark) column (41.4×250 mm, 8 μm, ODS-silica, Rainin) eluting at 45 ml per minute with a methanol-water 85:15 mixture, changing to 87:13 after 15 mins. Appropriate fractions were combined and evaporated under vacuum to yield the title compound as a white powder (52 mg). Mass and NMR spectra were fully consistent with the proposed structure.

EXAMPLE 53

5-(-Allylcarbamoyloximino)-25-cyclohexyl-22,23-dihydroavermectin B1 monosaccharide 5-oximino-25-cyclohexyl-22,23-dihydroavermectin B1 monosaccharide (Example 5) (500 mg) was reacted with allyl isocyanate (108 mg) in dichloromethane (50 ml) according to the method described in Example 43 to give the title compound as a white powder (352 mg). Mass and NMR spectra were fully consistent with the proposed structure.

What is claimed is:

1. A compound of formula (I)

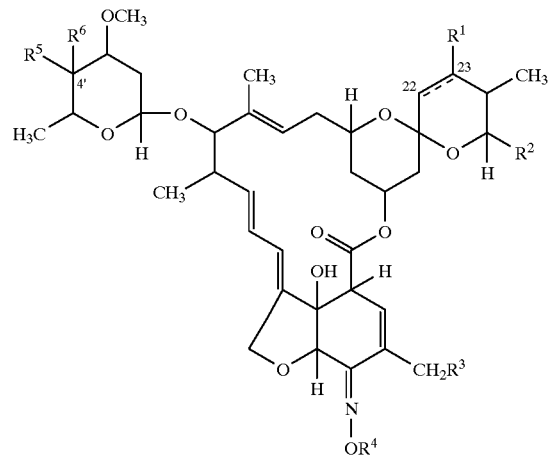

wherein the broken line at the 22-23 position represents an optional bond and either this bond is present and $R^1$ is absent or this bond is absent and $R^1$ is H or OH;

$R^2$ is a $C_1$–$C_8$ alkyl, or $C_3$–$C_8$ cycloalkyl group;

$R^3$ is H;

$R^4$ is H or a group capable of being hydrolyzed in vivo to yield a compound in which $R^4$ is H;

$R^5$ is OH; and $R^6$ is H.

2. A compound according to claim 1, in which said group capable of being hydrolyzed in vivo is an acetyl, t-butylcarbonyl, t-butyloxycarbonyl, benzoyl, methylpiperazinecarbonyl, N-methylcarbamoyl, N,N-dimethylcarbamoyl, formylphenylcarbamoyl, N-(4-diethylaminomethylphenyl)-carbamoyl, N-(4-methyl-1-piperazin-methylphenyl)-carbamoyl, N-(3-pyridylcarbonyl)-carbamoyl, N-(3-pyridyl)-carbamoyl or allylcarbamoyl, succinoyl, methoxysuccinoyl, 4-methylpiperazinesuccinoyl, pyrid-4-ylaminosuccinoyl, lysinyl or a N, N -bis(9-fluorenylmethoxy-carbonyl)lysinyl group.

3. A compound according to claim 1, in which R is cyclohexyl.

4. A compound according to claim 1, in which the optional bond at the 22-23 position is absent and $R^1$ is H.

5. 5-Oximino-22,23-dihydro-25-cyclohexylavermectin B1 monosaccharide.

6. A compound selected from the group consisting of:

5-oximino-22,23-dihydroavermectin B1 a monosaccharide;

5-oximino-25-cyclohexylavermectin B2 monosaccharide;

5-oximino-25-cyclohexylavermectin B1 monosaccharide;

5-(trimethylacetyloximino)-25-cyclohexyl-22,23-dihydroavermectin B1 monosaccharide;

5-(benzoyloximino)-25-cyclohexyl-22,23-dihydroavermectin B1 monosaccharide; p1 5-(N-methylcarbamoyloximino)-25-cyclohexyl-22,23-dihydroavermectin B1 monosaccharide;

5-(N,N-dimethylcarbamoyloximino)-25-cyclohexyl-22,23-dihydroavermectin B1 monosaccharide;

5-(4-methylpiperazinyl-1-carbonyloximino)-25-cyclohexyl-22,23-dihydroavermectin B1 monosaccharide;

5-(t-butyloxycarbonyloximino)-25-cyclohexyl-22,23-dihydroavermectin B1 monosaccharide;

5-(N-(4-formylphenyl)-carbamoyloximino)-25-cyclohexyl-22,23-dihydroavermectin B1 monosaccharide;

5-(N-(4-(diethylaminomethyl)phenyl)-carbamoyloximino)-25-cyclohexyl-22,23-dihydroavermectin B1 monosaccharide;

5-(N-(4-(4-methyl-1-piperazinyl-methyl)phenyl)-carbamoyloximino)-25-cyclohexyl-22,23-dihydroavermectin B1 monosaccharide;

5-(N-(3-pyridylcarbonyl)-carbamoyloximino)-25-cyclohexyl-22,23-dihydroavermectin B1 monosaccharide;

5-(N-(3-pyridyl)-carbamoyloximino)-25-cyclohexyl-22,23-dihydroavermectin B1 monosaccharide; and 5-(N-allylcarbamoyloximino)-25-cyclohexyl-22,23-dihydroavermectin B1 monosaccharide.

7. A pharmaceutical or veterinary composition, comprising a compound according to claim 1 and a pharmaceutically acceptable carrier or excipient.

8. A method of treatment of parasitic infections in an animal or human, which comprises administering to said animal or human an effective amount of a compound according to claim 1.

9. A process for preparing a compound of Formula I

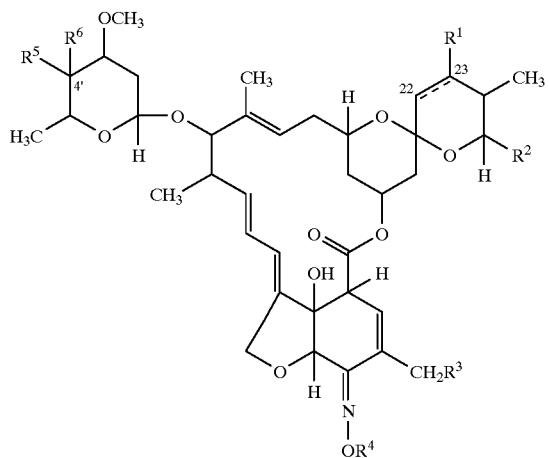

wherein the broken line at the 22-23 position represents an optional bond and either this bond is present and $R^1$ is absent or this bond is absent and $R^1$ is H or OH;

$R^2$ is a $C_1$–$C_8$ alkyl, or $C_3$–$C_8$ cycloalkyl group;

$R^3$ is H;

$R^4$ is H or a group capable of being hydrolyzed in vivo to yield a compound in which $R^4$ is H;

$R^5$ is OH; and $R^6$ is H;

which comprises the steps of (1) oxidizing a compound of formula II

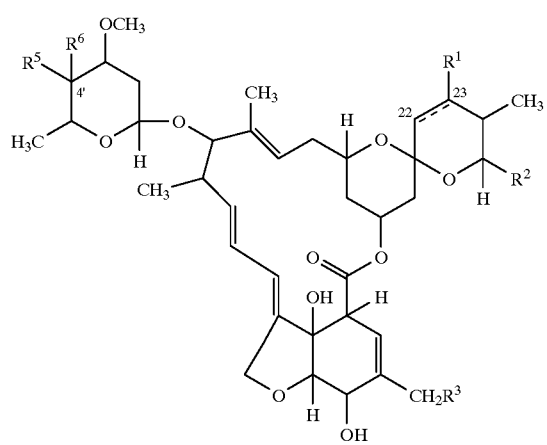

wherein the broken line, $R^1$, $R^2$, $R^3$ and $R^6$ are as defined above and $R^5$ is as defined above or $R^5$ is L-α-oleandrosyloxy and $R^6$ is H to yield a compound of formula III

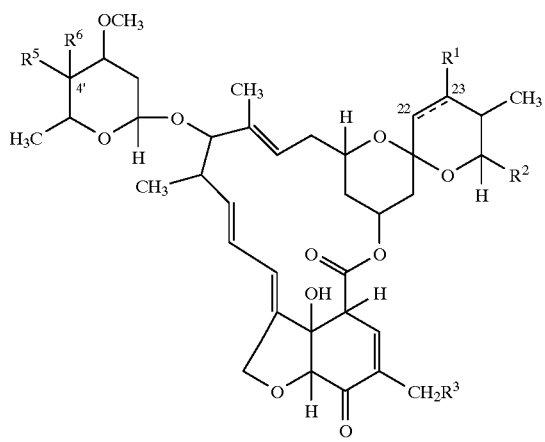

and (2) allowing the compound of formula (III) to react with a compound of formula $R^4$—O—$NH_2$ where $R^4$ is as defined above, and, where $R^5$ is α-oleandrosyloxy, hydrolyzing the compound obtained to yield a compound of formula (I).

10. A process according to claim 9 wherein group $R^4$ when H is replaced with said group capable of being hydrolyzed in vivo to yield a compound in which $R^4$ is H.

11. A process according to claim 9 wherein the compound of formula I obtained has a double bond at the 22-23 position and said compound is hydrogenated to reduce the double bond at the 22-23 position to a single bond.

* * * * *